Aug. 28, 1956 W. W. WAY Plant Pat. 1,508
VIOLA PLANT
Filed Oct. 31, 1955
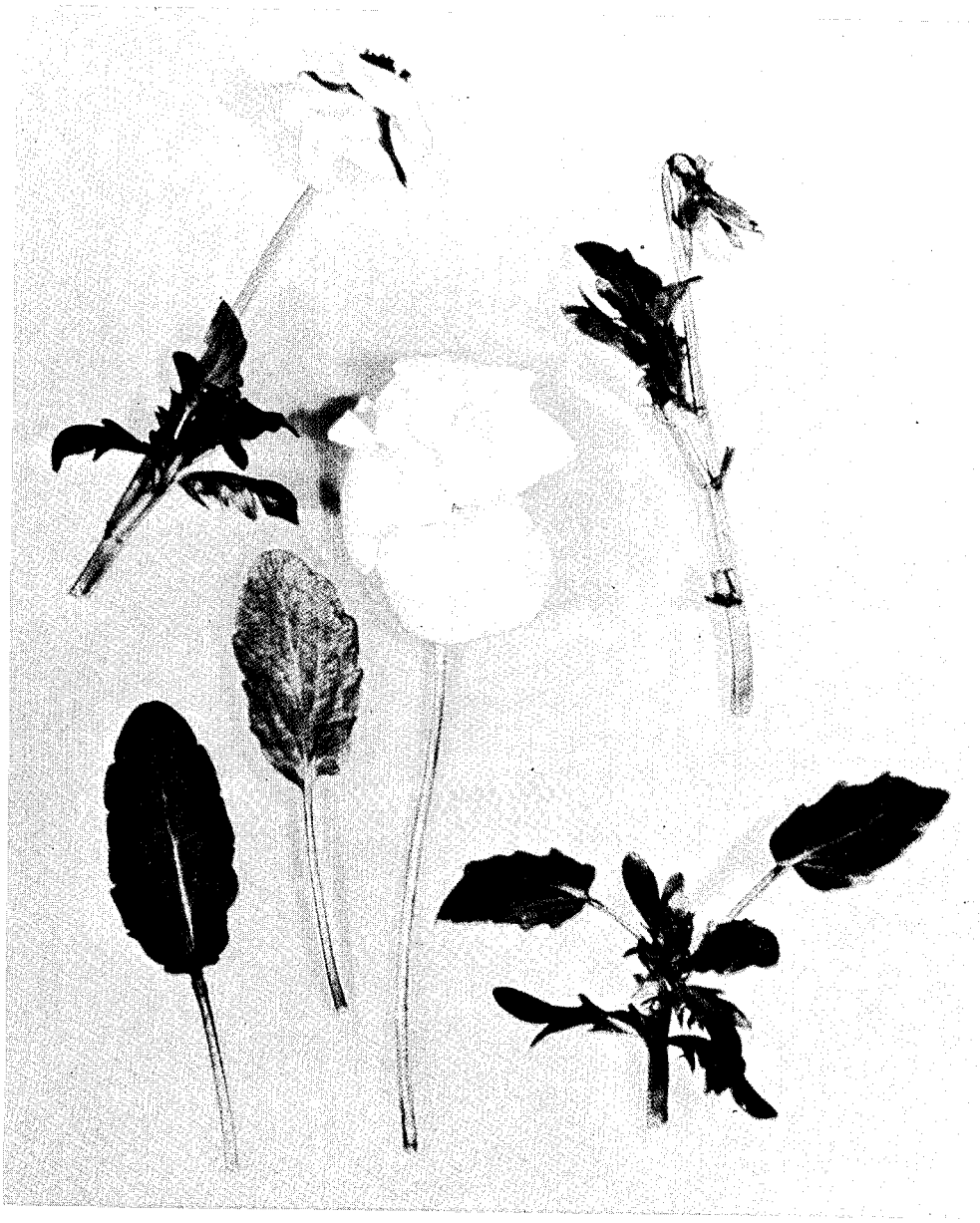
Inventor.
Walter W. Way, Deceased
By: Mabel P. Way, Executrix
By: Robb & Robb
Attorneys.

United States Patent Office

Plant Pat. 1,508
Patented Aug. 28, 1956

1,508

VIOLA PLANT

Walter Willard Way, deceased, late of Santa Barbara, Calif., by Mabel P. Way, executrix, Santa Barbara, Calif., assignor to Jackson & Perkins Company, Newark, N. Y., a corporation of New York Application October 31, 1955, Serial No. 544,099

1 Claim. (Cl. 47—60)

The present invention relates to a new and distinct variety of viola plant which was originated by me from the planting of seeds of the viola variety known as "Purple Heart" (Plant Patent No. 671).

My new viola plant is particularly characterized as to novelty and is distinguished from its parent variety, as well as from all other varieties of its class of which I am aware, by its low-growing habit of growth, its heavy and clean foliage, and its large white flowers which are borne on plants which are reblooming and perennial in climatic regions corresponding to up-State New York.

Asexual reproduction of my new variety by root divisions and cuttings, as performed in perennial blocks in a nursery at Newark, New York, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling of viola "Purple Heart."
Classification: Botanic—viola hybrid.

FLOWER (Observations made from plants grown outdoors at Newark, New York, in early October and about midmorning.)

Blooming habit: Recurrent; perennial in habit; blooms all season.

Bud:

*Size.*—Medium.

*Color.*—When sepals first divide—Light Dull Green-Yellow, Plate 17. When petals begin to unfurl—Pale Chalcedony Yellow, Plate 17. When half-blown: inside of petals—White, Plate 53, lightly overcast with Sea-Foam Yellow, Plate 31, with eye of Empire Yellow, Plate 4; reverse of petals—White, Plate 53, lightly overcast with Sea-Foam Yellow, Plate 31.

*Sepals.*—Branched; 5 in number. Color—Varley Green, Plate 18.

Bloom:

*Size.*—Large. Average size (when fully expanded): Length—from 3 inches to 3½ inches; width—from 2 inches to 2¼ inches.

*Stems.*—Medium length; from 5 inches to 6 inches in length; strong. Color—Mineral Green, Plate 18.

*Petalage.*—5 petals in number; petals medium thickness; not affected by hot or cold weather.

*Petals.*—Inside—velvety; outside—shiny.

*Color.*—2 upper petals—White, Plate 53, with eye of Empire Yellow, Plate 4; fluted. 2 side petals—White, Plate 53, with eye of Empire Yellow, Plate 4 and with base of Light Luminere Green, Plate 17, forming part of the eye. Lower petal: upper side—White, Plate 53; reverse side—White, Plate 53.

Fragrance: Moderate Viola fragrance.

Lasting quality: On the plant—long; as cut flower—long.

PLANT

Form: Low; flat.

Growth: Strong; generous.

Foliage: Heavy.

*Color.*—Upper side—Deep Dull Yellow Green (1), Plate 32; lower side—Light Bice Green, Plate 17.

*Shape.*—Ovoid.

*Veins.*—Color—Absinthe Green, Plate 31, with prominent center vein of lighter green color.

I claim:

A new and distinct variety of viola plant of the viola hybrid class, substantially as herein shown and described, characterized particularly as to novelty by its low-growing habit of growth, its heavy and clean foliage, and its large white flowers which are borne on plants which are reblooming and perennial in climatic regions corresponding to up-State New York.

No references cited.